(12) United States Patent
Liu et al.

(10) Patent No.: US 11,988,372 B2
(45) Date of Patent: May 21, 2024

(54) INFRARED LAMP TUBE HEAT DISSIPATION AUTOMATIC CONTROL SYSTEM

(71) Applicants: Chen Ya Liu, Taoyuan (TW); Chin Yuan Liu, Taoyuan (TW)

(72) Inventors: Chen Ya Liu, Taoyuan (TW); Chin Yuan Liu, Taoyuan (TW)

( * ) Notice: Subject to any disclaimer, the term of this patent is extended or adjusted under 35 U.S.C. 154(b) by 0 days.

(21) Appl. No.: 18/451,431

(22) Filed: Aug. 17, 2023

(65) Prior Publication Data
US 2024/0077194 A1 Mar. 7, 2024

(30) Foreign Application Priority Data
Sep. 6, 2022 (TW) .................................. 111133777

(51) Int. Cl.
| | |
|---|---|
| H03K 17/082 | (2006.01) |
| F21V 19/00 | (2006.01) |
| F21V 29/503 | (2015.01) |
| F21V 29/507 | (2015.01) |
| F21V 29/57 | (2015.01) |
| F21V 31/00 | (2006.01) |
| F21Y 103/10 | (2016.01) |

(52) U.S. Cl.
CPC ............ *F21V 29/57* (2015.01); *F21V 19/007* (2013.01); *F21V 29/503* (2015.01); *F21V 29/507* (2015.01); *F21V 31/005* (2013.01); *F21Y 2103/10* (2016.08)

(58) Field of Classification Search
CPC ...... F21V 29/57; F21V 19/007; F21V 29/503; F21V 29/507; F21V 31/005; F21Y 2103/10
See application file for complete search history.

(56) References Cited

U.S. PATENT DOCUMENTS

| | | | |
|---|---|---|---|
| 2015/0000877 A1* | 1/2015 | Yang | F28D 15/00 165/157 |
| 2018/0031223 A1* | 2/2018 | Mai | F21V 29/677 |
| 2020/0120838 A1* | 4/2020 | Arimura | H02M 7/48 |
| 2020/0267810 A1* | 8/2020 | Chemel | H05B 47/19 |

FOREIGN PATENT DOCUMENTS

CN 215135999 U * 12/2021

* cited by examiner

*Primary Examiner* — Elmito Breval
(74) *Attorney, Agent, or Firm* — Rosenberg, Klein & Lee

(57) ABSTRACT

An infrared lamp tube heat dissipation automatic control system, wherein, according to the temperature of the coolant in lamp tube and the value provided by the flow rate sensor, the controller calculates the optimal flow rate of the coolant in a proportional mode that the higher the temperature, the faster the flow rate, and then control the flow rate by the flow control valve, so as to achieve predetermined coolant temperature and perform contact heat dissipation to the halogen bulb, thus solving the problem of the non-contact heat dissipation of halogen bulb of the prior art that cannot achieve the predetermined heat dissipation effect and resulting in the easy damage of halogen bulb; and further improves the product reliability and the service life. Furthermore, the leakproof structure of the lamp holder achieves a completely leakproof function, thereby enhancing product safety.

9 Claims, 10 Drawing Sheets

INFRARED LAMP TUBE HEAT DISSIPATION AUTOMATIC CONTROL SYSTEM

BACKGROUND OF THE INVENTION

1. Field of the Invention

An infrared lamp tube heat dissipation automatic control system, especially one that calculates the optimal flow rate of the coolant in a proportional mode that the higher the temperature, the faster the flow rate, and perform contact heat dissipation to the halogen bulb.

2. Description of the Related Art

Infrared rays will penetrate into the depths of the human skin for 40 mm, by promoting the resonance of human cell molecules, charged and movement to expand the blood vessels, making blood circulation smooth and generate self-heating, and also increase the temperature of the deep body and improve metabolism, activate cell tissue, promote the excretion of toxins and wastes in the body and relieves fatigue. When the temperature of the body part increased, it can inhibit the proliferation of cancer cells and activate the immune system. As the body temperature rises with 1° C., the immune system is activated 5 to 6 times. Therefore, by increasing the temperature of the body part, it can relieve pain and prevent the proliferation of cancer cells, and activate the immune system to reduce cancer cells.

Also, the infrared rays are irradiated mostly by the halogen bulbs, to achieve the irradiation effect; however, some halogen bulbs have an operating temperature about 324.4 Celsius degrees, so the heat dissipation of the infrared lamps composed of halogen lamps becomes important issue.

Taiwan Patent No. M610319, An infrared device with fluid heat dissipation, comprising: the body is a long body made of aluminum extrusion, and the section of the body is concave so that the two ends of the body form two concave end surfaces, and an accommodating space is formed inside the body, At least one fluid channel is provided between the concave end faces with the accommodating space as the center, and each halogen lamp is located in the accommodating space, so that the side position of each halogen lamp corresponds to the side position of the fluid channel, forming each There is a barrier between the halogen lamp and the fluid channel, and the filter is statically placed in the accommodating space; thereby, when the halogen lamp emits full-wavelength colored light through the filter, the color temperature of the full-wavelength colored light is changed, and the filter Infrared color light is emitted to the outside of the light guide plate, and is separated from the halogen lamp by a barrier with the fluid in the fluid channel, so that the fluid flows to perform non-contact heat dissipation on the halogen lamp.

However, although having non-contact heat dissipation, the working temperature of the halogen lamp is too high, non-contact heat dissipation for halogen lamps is not easy to achieve the desired heat dissipation effect, and after the high temperature of halogen lamps accumulating for a long time, it will greatly affect the service life and reliability of halogen lamps. Thus, solving the heat dissipation problem on the halogen lamp problem of the infrared lamp tube becomes the subject of this present invention.

SUMMARY OF THE INVENTION

A primary objective of the present invention is to provide an infrared lamp tube heat dissipation automatic control system, using the flowing coolant directly contact cool the halogen lamp, and calculates the optimal flow rate of the coolant in a proportional mode that the higher the temperature, the faster the flow rate, so as to achieve the most effective mode of heat dissipation, thereby improving product reliability and the service life.

In order to achieve the above objective, the present invention, including: an elongated housing, whose section is concave to form an accommodating space, the bottom of the elongated housing is provided with at least one installation hole; at least one lamp holder corresponding to the installation hole arranged at the bottom of the elongated housing; at least one halogen bulb arranged on the lamp holder, and the upper section of the halogen bulb protrudes into the accommodating space; a light-transmitting board arranged on the top of the elongated housing; two left and right covers arranged on the left and right sides of the elongated housing respectively, and a flow hole is provided on the two left and right covers relative to the accommodating space; wherein the infrared lamp tube further includes an automatic control system for heat dissipation, and the automatic control system for heat dissipation includes: a circulation line, which includes an input end and an output end, respectively connected to the flow holes of the right and left covers, for injecting coolant into the accommodating space of the infrared lamp tube and circulating it, so as to cool down the halogen bulb; a temperature sensor is arranged in the infrared lamp tube to detect the temperature of the coolant in the accommodating space; a controller, including a microprocessor and a memory, is electrically connected to the temperature sensor, and calculates the temperature of the coolant; a flow rate sensor, arranged on the circulation line to detect the flow rate of the coolant and transmit the value to the controller; a flow control valve, including a first control valve and a driving unit, the driving unit receives an instruction signal from the controller to control the first control valve to adjust its flow; a pump, installed on the circulation line and electrically connected to the controller, for pumping the coolant to circulate; a cooling device, installed on the circulation line, to lower the temperature of the coolant flowing out from the output end; and according to the temperature of the coolant in the accommodating space and the value provided by the flow rate sensor, the controller calculates the optimal flow rate of the coolant in a proportional mode that the higher the temperature, the faster the flow rate, and then control the flow rate by the flow control valve, so as to achieve predetermined coolant temperature and perform contact heat dissipation to the halogen bulb.

Also, the driving unit of the flow control valve is composed of an electromagnetic solenoid, a micro motor or a piezoelectric unit.

Also, the flow rate sensor and the flow control valve include independent structures or combined structures.

Also, the present invention further includes an external supply liquid entering the cooling device or the circulation line through a supply tube, and the supply tube is provided with a second control valve, the second control valve is electrically connected to the controller.

Also, the left and right covers are further locked on both sides of the elongated housing by multiple screws, and the left and right covers further include a sealing gasket.

Also, the light-transmitting board further includes two joint strips respectively pressed and fixed on the front and rear sides of the light-transmitting board, so that the light-transmitting board is fixed on the top of the elongated housing.

Also, the light-transmitting board is composed of a light guide plate.

Also, in a preferred embodiment, the installation hole of the elongated housing is a screw hole, and the lamp holder includes: a hollow seat, having a ring shaped body formed on the top thereof, a protruding thread body that can be locked in the installation hole is formed on the ring shaped body, a first through hole is formed in the protruding thread body, below the first through hole is connected with a second through hole with a larger diameter, and an internal screw thread is formed at the bottom of the second through hole; an O-ring washer, which is sleeved on the bottom of the outer peripheral edge of the protruding thread body, and is pressed against the bottom edge of the elongated housing by the ring shaped body; a waterproof plug, which is tightly placed in the second through hole, the upper part of the waterproof plug is provided with a receiving hole for the lower part of the halogen bulb to be embedded, and an electrical pin of the halogen bulb protrude out the bottom of the waterproof plug; and an internal nut, which is locked in an internal screw thread at the bottom of the second through hole, for pressing the upper part of the waterproof plug against the bottom edge surface of the first through hole, so that the first through hole forms a waterproof closed state, and the internal nut has a third through hole.

Also, the waterproof plug is made of elastic material, the receiving hole is matched with the shape of the lower part of the halogen bulb, so that it can be combined into a tight fit, and the bottom of the receiving hole is provided with two small perforations for letting the electrical pin of the halogen bulb protrude and locate in the third through hole.

With the features above disclosed, according to the temperature of the coolant in the accommodating space and the value provided by the flow rate sensor, the automatic control system for heat dissipation calculates the optimal flow rate of the coolant in a proportional mode that the higher the temperature, the faster the flow rate, and then control the flow rate by the flow control valve, so as to achieve the most effective mode of heat dissipation, then perform contact heat dissipation to the halogen bulb, so as to solve the problem of the non-contact heat dissipation of halogen bulb of the prior art that cannot achieve the predetermined heat dissipation effect and resulting in the easy damage of halogen bulb; and further improves the product reliability and the service life. Furthermore, the leakproof structure of the lamp holder achieves a completely leakproof function, thereby enhancing product safety.

DETAILED DESCRIPTION OF THE PREFERRED EMBODIMENT

Figure 1:
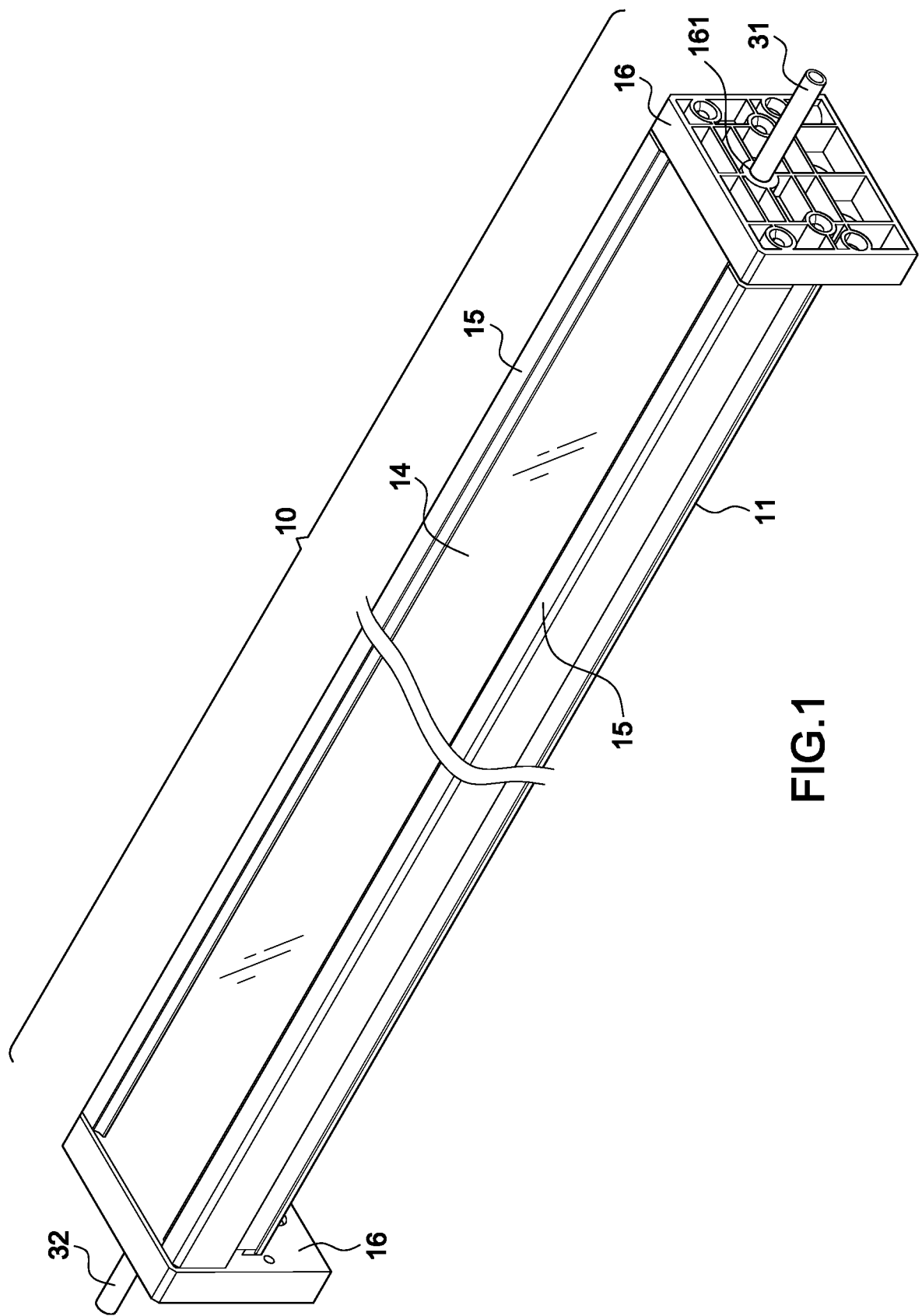
FIG. 1 is a top perspective view of the infrared lamp tube of the present invention.
Figure 2:
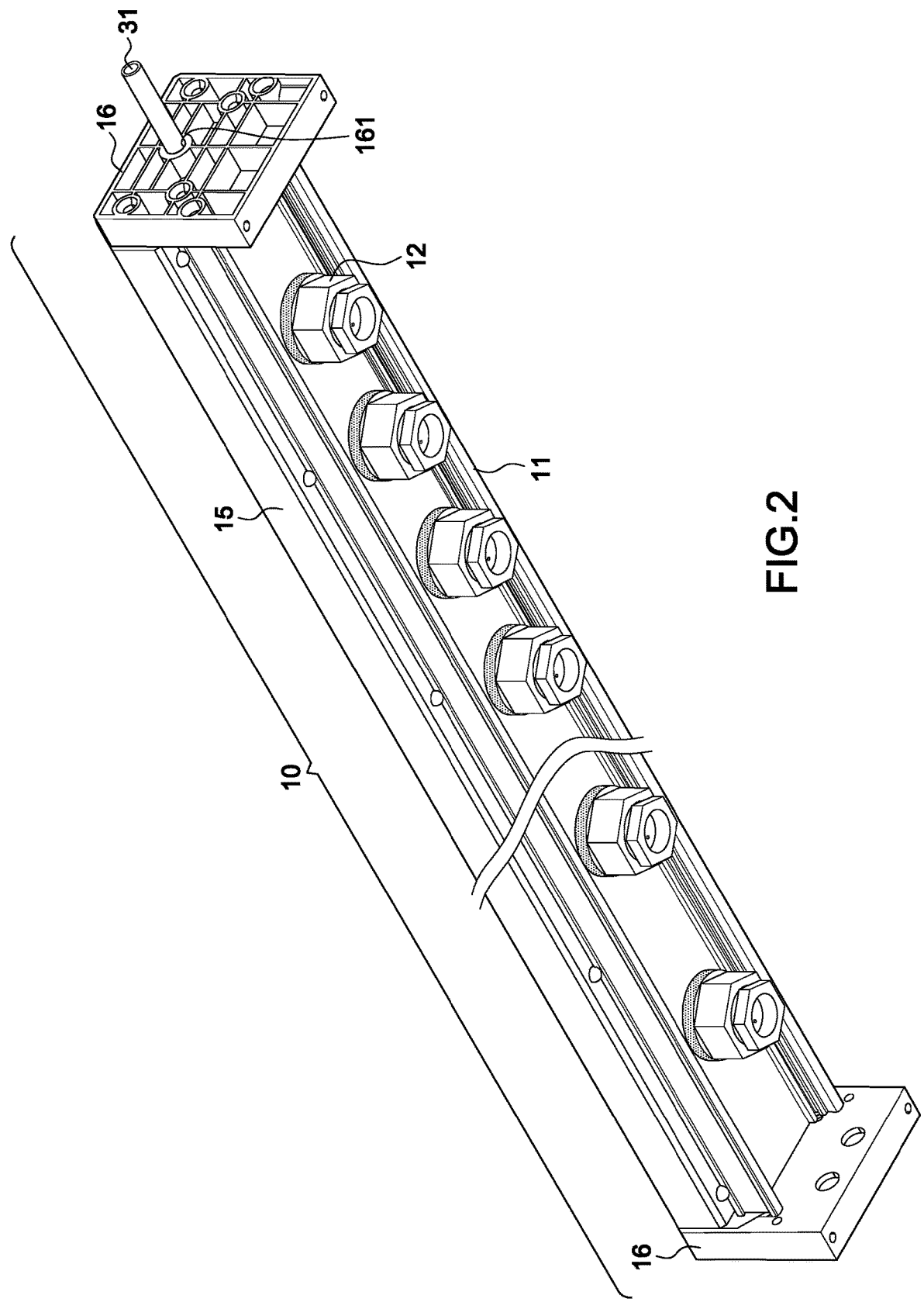
FIG. 2 is a bottom perspective view of the infrared lamp tube of the present invention.

Referring to FIGS. 1-8, the applicable embodiment of the infrared lamp tube heat dissipation automatic control system of the present invention, the infrared lamp tube 10 including: an elongated housing 11, whose section is concave to form an accommodating space 111, the bottom of the elongated housing 11 is provided with at least one installation hole 112; at least one lamp holder 12 corresponding to the installation hole 112 arranged at the bottom of the elongated housing 11; at least one halogen bulb 13 arranged on the lamp holder 12, and the upper section of the halogen bulb 13 protrudes into the accommodating space 111.

A light-transmitting board 14 arranged on the top of the elongated housing 11. In this embodiment, the light-transmitting board 14 is composed of a light guide plate, includes two joint strips 15 respectively pressed and fixed on the front and rear sides of the light-transmitting board 14, so that the light-transmitting board 4 is fixed on the top of the elongated housing 11.

Figure 3:
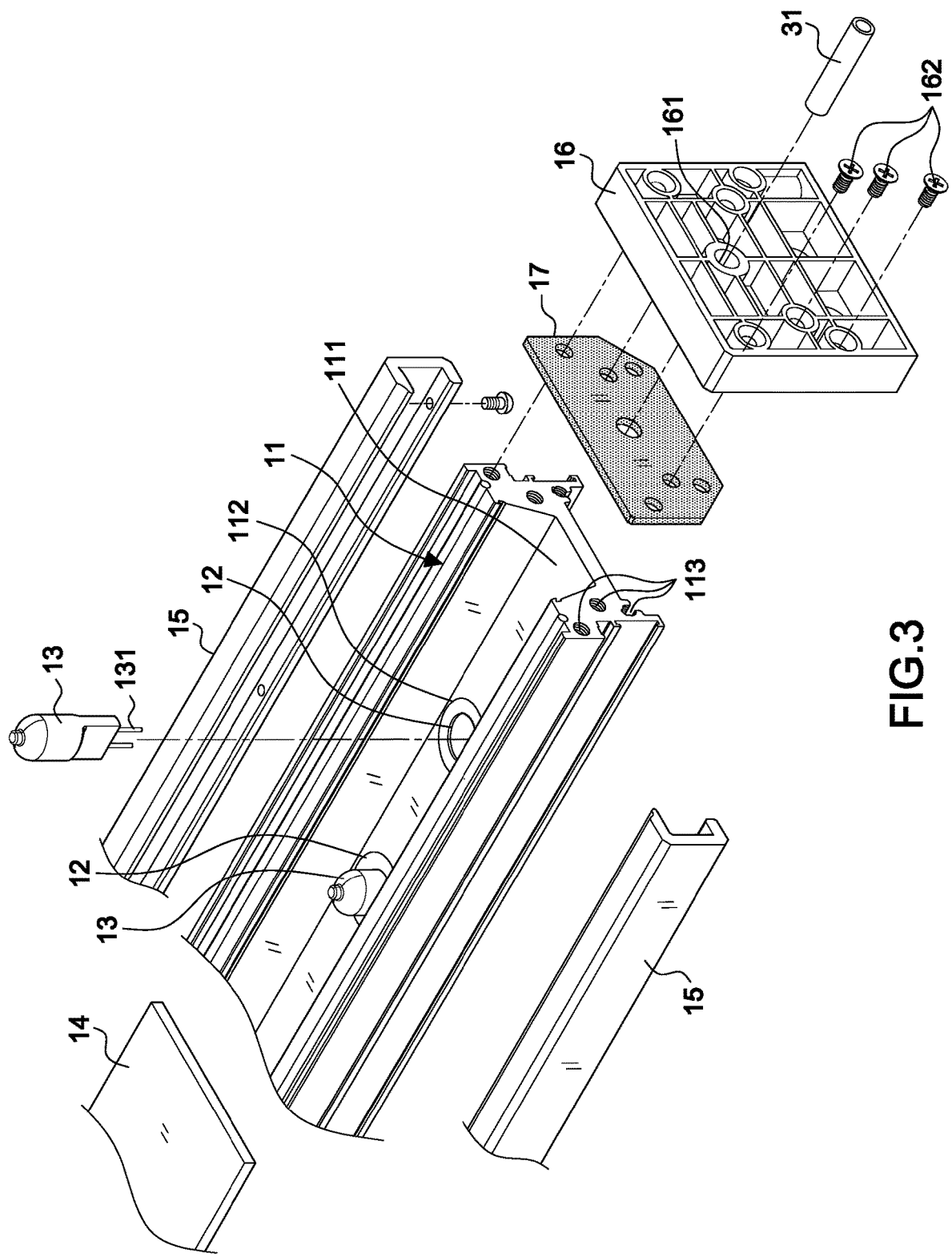
FIG. 3 is an exploded perspective view of a part structure of the infrared lamp tube of the present invention.
Figure 4:
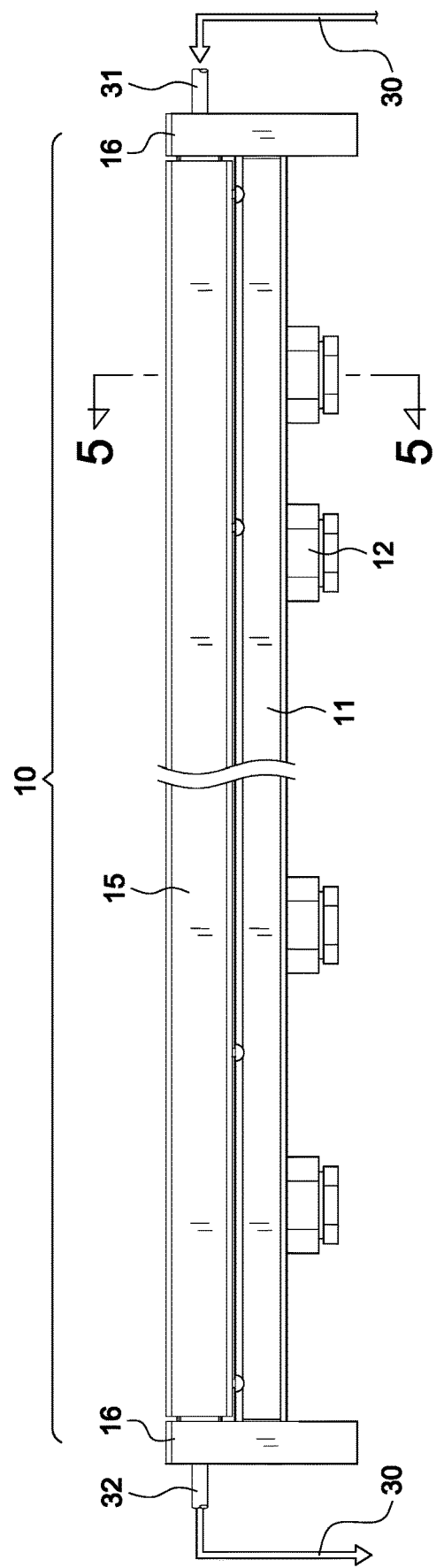
FIG. 4 is a side view of the infrared lamp tube of the present invention.
Figure 5:
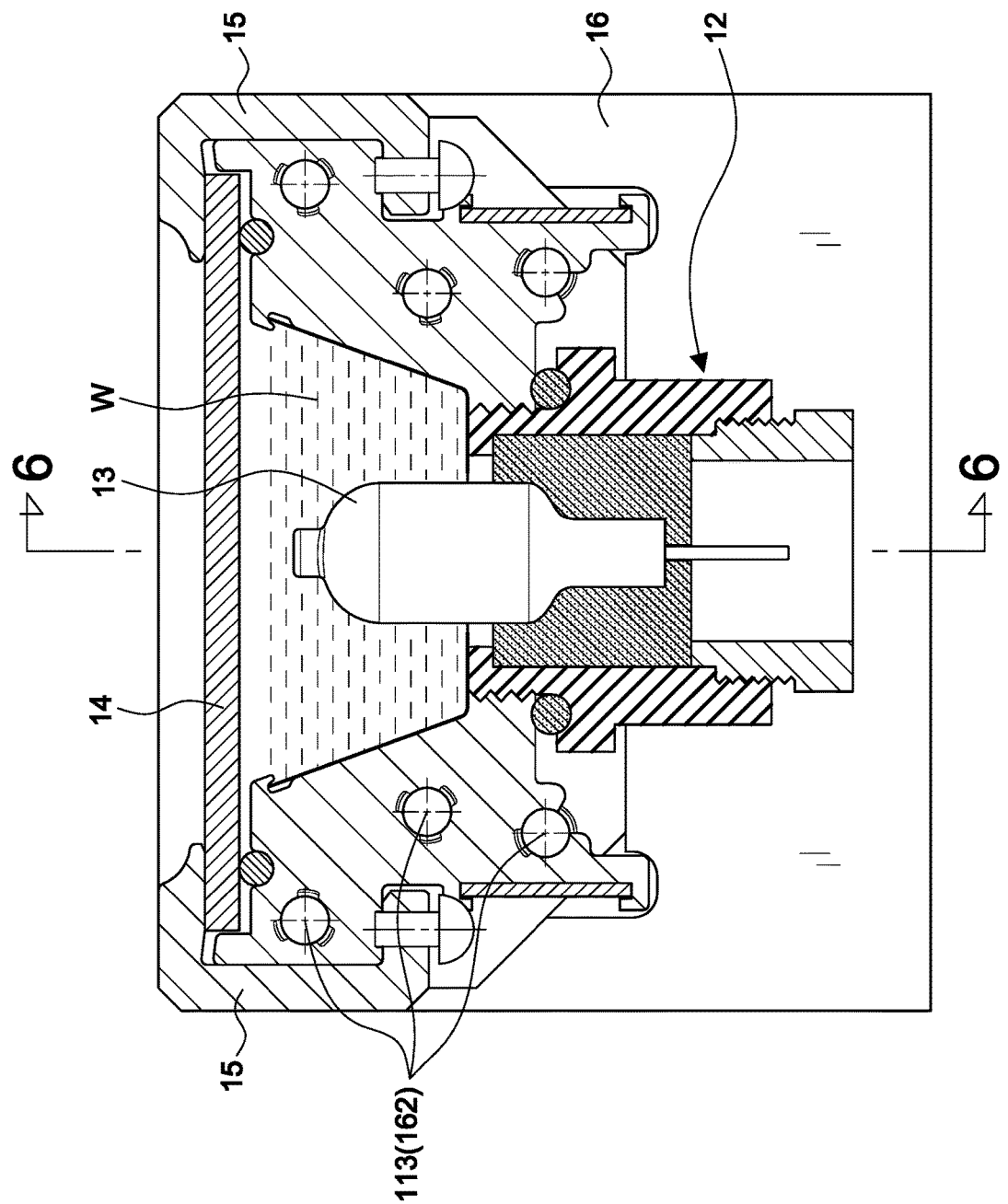
FIG. 5 is a sectional view along line 5-5 in FIG. 4.
Figure 6:
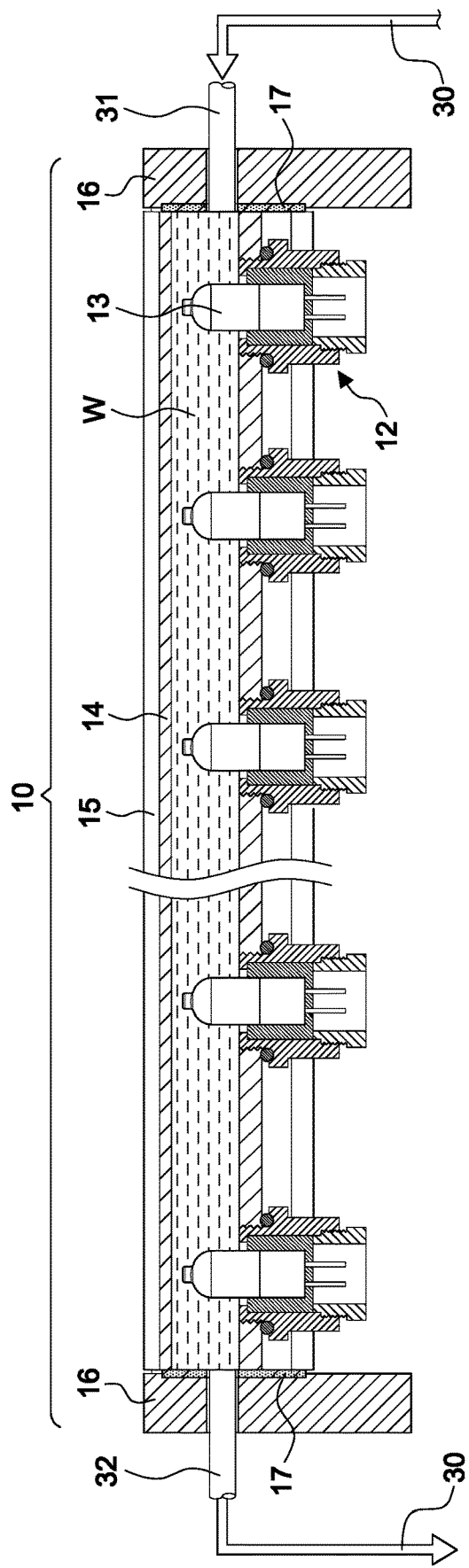
FIG. 6 is a sectional view along line 6-6 in FIG. 5.

Two left and right covers 16 arranged on the left and right sides of the elongated housing 11 respectively, and a flow hole 161 is provided on the two left and right covers 16 relative to the accommodating space 111; referring to FIG. 3, in this embodiment, the left and right covers 16 are further locked on a fixing hole 113 of both sides of the elongated housing 11 by multiple screws 162, and the inner side of the left and right covers 16 further include a sealing gasket 17, but not limited to this.

Figure 7:
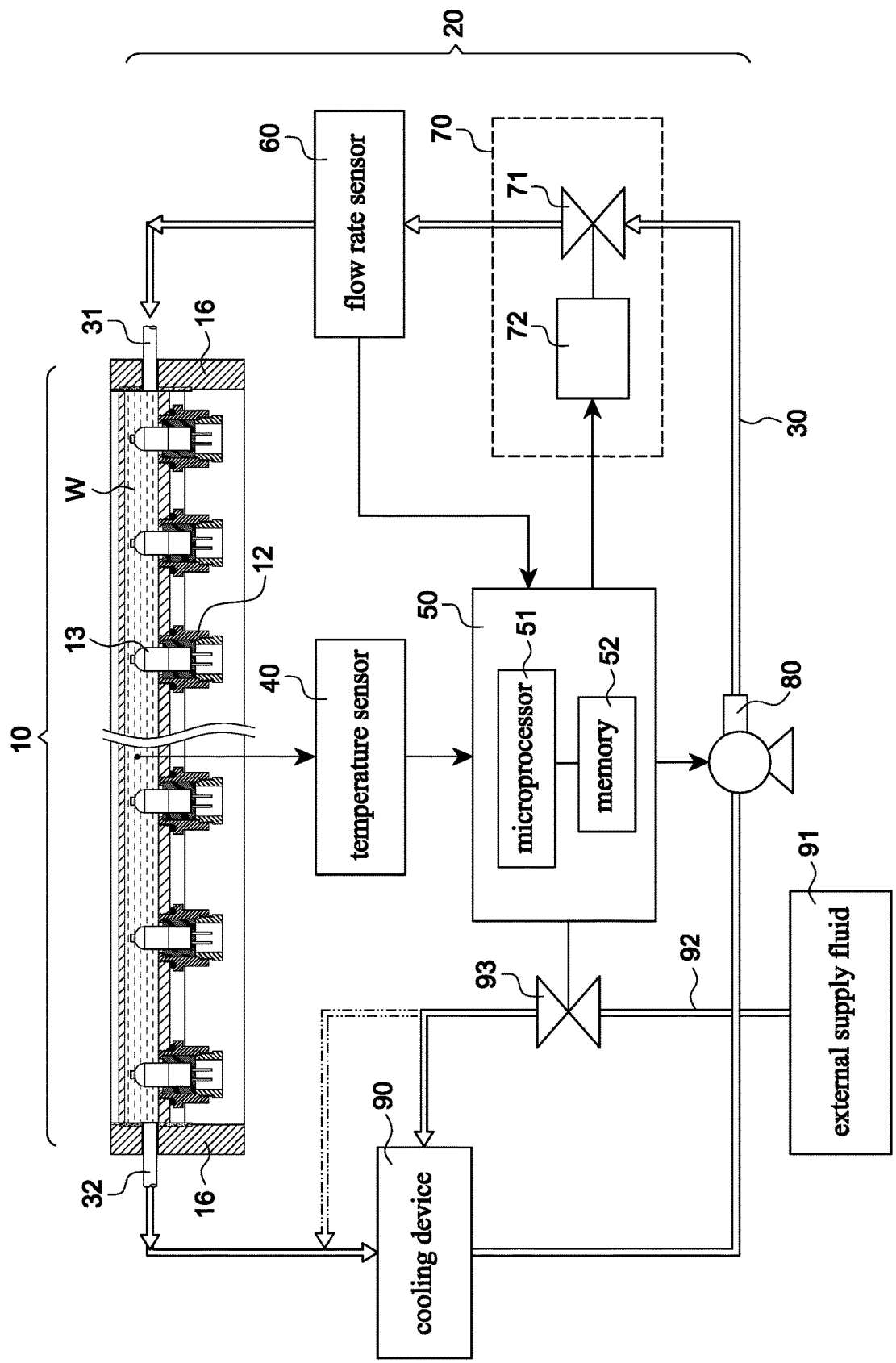
FIG. 7 is a schematic diagram illustrating of the structure of an applicable embodiment of the present invention.

Referring to FIG. 7, the infrared lamp tube 10 further includes an automatic control system for heat dissipation 20, and the automatic control system for heat dissipation 20 includes:

A circulation line 30, which includes an input end 31 and an output end 32, respectively connected to the flow holes 161 of the right and left covers 16, for injecting coolant W into the accommodating space 111 of the infrared lamp tube 10 and circulating it, so as to cool down the halogen bulb 13.

A temperature sensor 40 is arranged in the infrared lamp tube 10 to detect the temperature of the coolant W in the accommodating space 111; a controller 50, including a microprocessor 51 and a memory 52, is electrically connected to the temperature sensor 40, and calculates the temperature of the coolant W;

A flow rate sensor 60, arranged on the circulation line 30 to detect the flow rate of the coolant W and transmit the value to the controller 50; In this embodiment, the flow rate sensor 60 can be composed of a velocity meter or a flow meter. If using the velocity meter, the flow rate of the coolant W can be directly measured; If using flow meter, the controller 50 can calculates the flow rate of the coolant W through the cross-sectional area of the circulation line 30; Such flow rate sensor 60 is already commercially mature products, so the feature of it is not described in detail here.

A flow control valve 70, including a first control valve 71 and a driving unit 72, the driving unit 72 receives an instruction signal from the controller 50 to control the first control valve 71 to adjust the flow rate; In this embodiment, the driving unit 72 of the flow control valve 70 is composed of an electromagnetic solenoid, a micro motor or a piezoelectric unit. Such flow control valve 70 is already commercially mature products, so the feature of it is not described in detail here. The flow rate sensor 60 and the flow control valve 70 include independent structures or combined structures.

A pump 80, installed on the circulation line 30 and electrically connected to the controller 50, for pumping the coolant W to circulate; A cooling device 90, installed on the circulation line 30, to lower the temperature of the coolant W flowing out from the output end 32; and in this embodiment, the cooling device 90 includes a heat exchanger.

Figure 8:
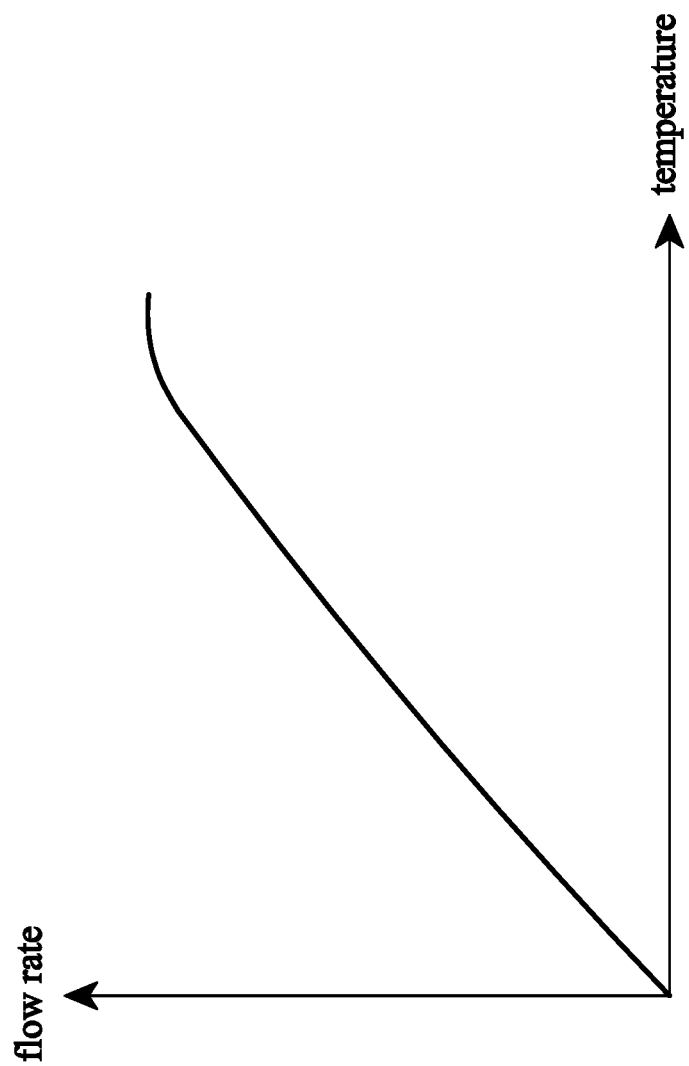
FIG. 8 is a curve diagram illustrating the relation of the flow rate and the temperature of the coolant of the present invention.

Whereby, according to the temperature of the coolant W in the accommodating space 111 and the value provided by the flow rate sensor 60, as FIG. 8 showing, the controller 50 calculates the optimal flow rate of the coolant W in a proportional mode that the higher the temperature, the faster the flow rate, and then control the flow rate by the flow control valve 70, so as to achieve predetermined coolant W temperature and perform contact heat dissipation to the halogen bulb 13.

Referring to FIG. 7, the present invention further includes an external supply liquid 91 entering the cooling device 90 or the circulation line 30 through a supply tube 92, and the supply tube 92 is provided with a second control valve 93, the second control valve 93 is electrically connected to the controller 50.

Figure 9:
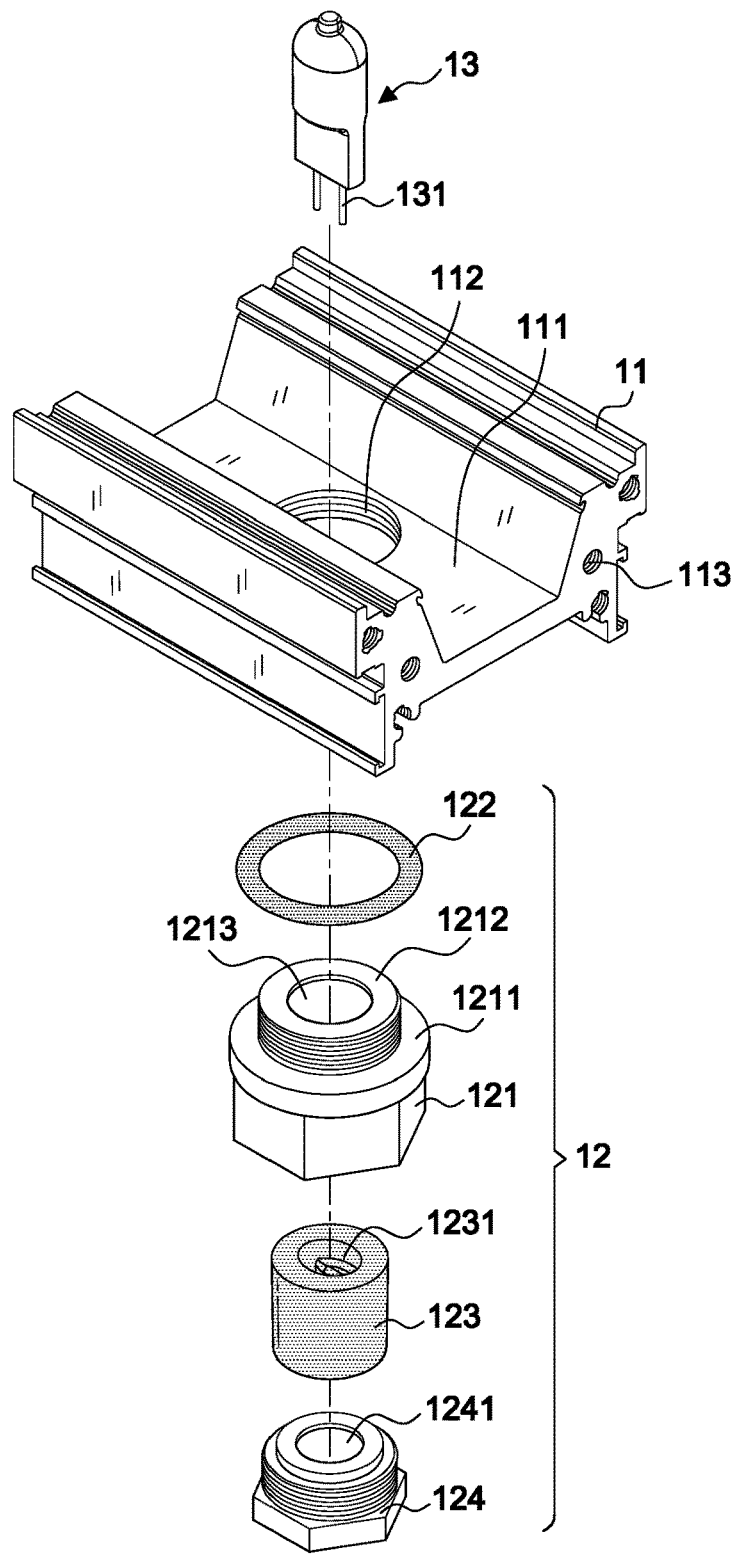
FIG. 9 is an exploded perspective view of the leakproof structure of the lamp holder of the present invention.
Figure 10:
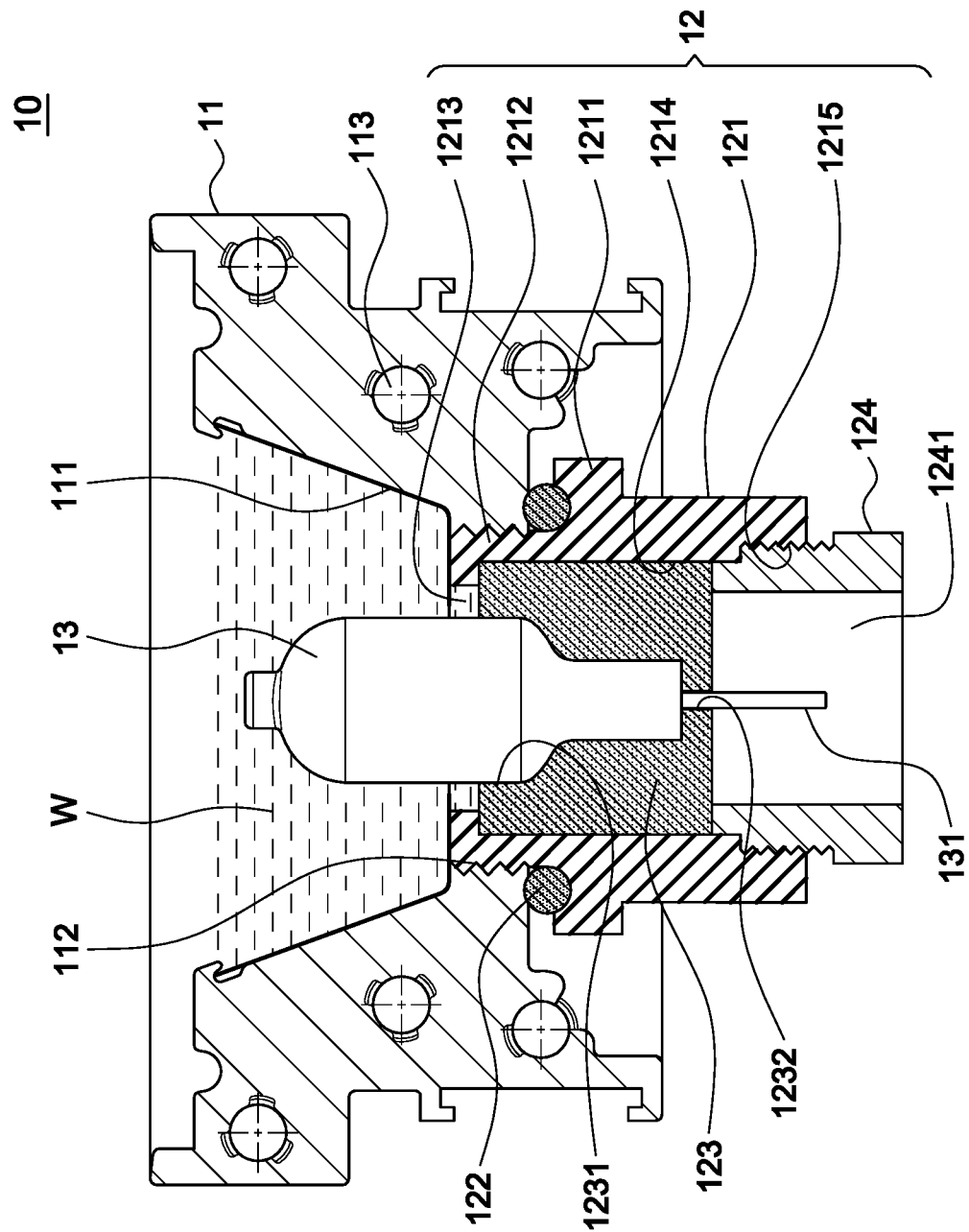
FIG. 10 is a sectional view of the leakproof structure of the lamp holder of the present invention.

Also, in order to prevent the coolant W from leaking caused by the flow rate of the coolant W entering and exiting the accommodating space 111, the present invention further includes a leakproof structure of the lamp holder 12. Referring to FIGS. 9~10, in an applicable embodiment, the installation hole 112 of the elongated housing 11 is a screw hole, and the lamp holder 12 includes: a hollow seat 121, having a ring shaped body 1211 formed on the top thereof, a protruding thread body 1212 that can be locked in the installation hole 112 is formed on the ring shaped body 1211, a first through hole 1213 is formed in the protruding thread body 1212, below the first through hole 1213 is connected with a second through hole 1214 with a larger diameter, and an internal screw thread 1215 is formed at the bottom of the second through hole 1214; an O-ring washer 122, which is sleeved on the bottom of the outer peripheral edge of the protruding thread body 1212, and is pressed against the bottom edge of the elongated housing 11 by the ring shaped body 1211; a waterproof plug 123, which is tightly placed in the second through hole 1214, the upper part of the waterproof plug 123 is provided with a receiving hole 1231 for the lower part of the halogen bulb 13 to be embedded, and an electrical pin 131 of the halogen bulb 13 protrude out the bottom of the waterproof plug 123; and an internal nut 124, which is locked in an internal screw thread 1215 at the bottom of the second through hole 1214, for pressing the upper part of the waterproof plug 123 against the bottom edge surface of the first through hole 1213, so that the first through hole 1213 forms a waterproof closed state, and the internal nut 124 has a third through hole 1241.

In this embodiment, the waterproof plug 123 is made of elastic material, the receiving hole 1231 is matched with the shape of the lower part of the halogen bulb 13, so that it can be combined into a tight fit, and the bottom of the receiving hole 1231 is provided with two small perforations 1232 for letting the electrical pin 131 of the halogen bulb 13 protrude and locate in the third through hole 1241.

With the structure disclosed above, first, the lamp holder 12 is combined with the installation hole 112, and has an excellent sealing effect, which can ensure that the coolant W in the accommodating space 111 will not leaks out from the installation hole 112; moreover, the lower section of the halogen bulb 13 is covered by the waterproof plug 123 in a tight state; in this way, the present invention achieves a complete leakproof structure.

With the features above disclosed, according to the temperature of the coolant W in lamp tube and the value provided by the flow rate sensor 60, the controller 50 calculates the optimal flow rate of the coolant W in a proportional mode that the higher the temperature, the faster the flow rate, and then control the flow rate by the flow control valve 70, so as to achieve predetermined coolant W temperature and perform contact heat dissipation to the halogen bulb 13, thus solving the problem of the non-contact heat dissipation of halogen bulb of the prior art that cannot achieve the predetermined heat dissipation effect and resulting in the easy damage of halogen bulb; and further improves the product reliability and the service life. Furthermore, the leakproof structure of the lamp holder 12 achieves a completely leakproof function, thereby enhancing product safety.

Although particular embodiments of the invention have been described in detail for purposes of illustration, various modifications and enhancements may be made without departing from the spirit and scope of the invention. Accordingly, the invention is not to be limited except as by the appended claims.

What is claimed is:
1. An infrared lamp tube heat dissipation automatic control system, including:
   an elongated housing, whose section is concave to form an accommodating space, the bottom of the elongated housing is provided with at least one installation hole;
   at least one lamp holder corresponding to the installation hole arranged at the bottom of the elongated housing;
   at least one halogen bulb arranged on the lamp holder, and the upper section of the halogen bulb protrudes into the accommodating space;
   a light-transmitting board arranged on the top of the elongated housing;
   two left and right covers arranged on the left and right sides of the elongated housing respectively, and a flow hole is provided on the two left and right covers relative to the accommodating space;
   wherein the infrared lamp tube further includes an automatic control system for heat dissipation, and the automatic control system for heat dissipation includes:
   a circulation line, which includes an input end and an output end, respectively connected to the flow holes of the right and left covers, for injecting coolant into the accommodating space of the infrared lamp tube and circulating it, so as to cool down the halogen bulb;
   a temperature sensor is arranged in the infrared lamp tube to detect the temperature of the coolant in the accommodating space;
   a controller, including a microprocessor and a memory, is electrically connected to the temperature sensor, and calculates the temperature of the coolant;
   a flow rate sensor, arranged on the circulation line to detect the flow rate of the coolant and transmit the value to the controller;
   a flow control valve, including a first control valve and a driving unit, the driving unit receives an instruction signal from the controller to control the first control valve to adjust its flow;
   a pump, installed on the circulation line and electrically connected to the controller, for pumping the coolant to circulate;

a cooling device, installed on the circulation line, to lower the temperature of the coolant flowing out from the output end; and according to the temperature of the coolant in the accommodating space and the value provided by the flow rate sensor, the controller calculates the optimal flow rate of the coolant in a proportional mode that the higher the temperature, the faster the flow rate, and then control the flow rate by the flow control valve, so as to achieve predetermined coolant temperature and perform contact heat dissipation to the halogen bulb.

2. The infrared lamp tube heat dissipation automatic control system as claimed in claim 1, wherein the driving unit of the flow control valve is composed of an electromagnetic solenoid, a micro motor or a piezoelectric unit.

3. The infrared lamp tube heat dissipation automatic control system as claimed in claim 2, wherein the flow rate sensor and the flow control valve include independent structures or combined structures.

4. The infrared lamp tube heat dissipation automatic control system as claimed in claim 1, wherein further includes an external supply liquid entering the cooling device or the circulation line through a supply tube, and the supply tube is provided with a second control valve, the second control valve is electrically connected to the controller.

5. The infrared lamp tube heat dissipation automatic control system as claimed in claim 1, wherein the left and right covers are further locked on both sides of the elongated housing by multiple screws, and the left and right covers further include a sealing gasket.

6. The infrared lamp tube heat dissipation automatic control system as claimed in claim 1, wherein the light-transmitting board further includes two joint strips respectively pressed and fixed on the front and rear sides of the light-transmitting board, so that the light-transmitting board is fixed on the top of the elongated housing.

7. The infrared lamp tube heat dissipation automatic control system as claimed in claim 1, wherein the light-transmitting board is composed of a light guide plate.

8. The infrared lamp tube heat dissipation automatic control system as claimed in claim 1, wherein the installation hole of the elongated housing is a screw hole, and the lamp holder includes:

a hollow seat, having a ring shaped body formed on the top thereof, a protruding thread body that can be locked in the installation hole is formed on the ring shaped body, a first through hole is formed in the protruding thread body, below the first through hole is connected with a second through hole with a larger diameter, and an internal screw thread is formed at the bottom of the second through hole;

an O-ring washer, which is sleeved on the bottom of the outer peripheral edge of the protruding thread body, and is pressed against the bottom edge of the elongated housing by the ring shaped body;

a waterproof plug, which is tightly placed in the second through hole, the upper part of the waterproof plug is provided with a receiving hole for the lower part of the halogen bulb to be embedded, and an electrical pin of the halogen bulb protrude out the bottom of the waterproof plug; and an internal nut, which is locked in an internal screw thread at the bottom of the second through hole, for pressing the upper part of the waterproof plug against the bottom edge surface of the first through hole, so that the first through hole forms a waterproof closed state, and the internal nut has a third through hole.

9. The infrared lamp tube heat dissipation automatic control system as claimed in claim 8, wherein the waterproof plug is made of elastic material, the receiving hole is matched with the shape of the lower part of the halogen bulb, so that it can be combined into a tight fit, and the bottom of the receiving hole is provided with two small perforations for letting the electrical pin of the halogen bulb protrude and locate in the third through hole.

\* \* \* \* \*